United States Patent [19]

Engelhardt et al.

[11] Patent Number: 4,731,369

[45] Date of Patent: Mar. 15, 1988

[54] AMIDES AND ESTERS OF 2-(N-(HYDROXYPIPERIDINOALKYL) AND (HYDROXYPYRROLIDINOALKYL)-AMINOSULFONYL)-6-NITROBENZOIC ACIDS USEFUL AS ADJUNCTS TO RADIATION THERAPY

[75] Inventors: Edward L. Engelhardt, Gwynedd Valley; Walfred S. Saari, Lansdale, both of Pa.

[73] Assignee: Merck & Co. Inc., Rahway, N.J.

[21] Appl. No.: 68,814

[22] Filed: Jun. 26, 1987

Related U.S. Application Data

[63] Continuation of Ser. No. 795,567, Nov. 6, 1985, abandoned.

[51] Int. Cl.$^4$ ................. C07D 207/12; C07D 211/40; A61K 31/445; A61K 31/40
[52] U.S. Cl. ..................................... 514/327; 514/328; 514/331; 514/424; 514/245; 514/428; 548/543; 548/544; 548/546; 548/550; 548/556; 548/567; 548/569; 546/232; 546/233; 546/235; 546/220; 546/221

[58] Field of Search ............... 514/327, 328, 331, 424, 514/425, 428; 548/543, 544, 546, 550, 556, 567, 569; 546/232, 233, 235, 220, 221

[56] References Cited

U.S. PATENT DOCUMENTS

| 4,132,786 | 1/1979 | Moreau et al. | 546/232 |
| 4,396,622 | 8/1983 | Jozic | 546/232 |
| 4,603,133 | 7/1986 | Engelhardt et al. | 514/229 |

OTHER PUBLICATIONS

Wardman, Radiat. Phys, Chem., vol. 24, pp. 293-305 (1984).

*Primary Examiner*—John M. Ford
*Attorney, Agent, or Firm*—R. D. Meredith; S. B. Abrams; H. J. Pfeiffer

[57] ABSTRACT

Amides and esters of 2-[N-(hydroxypiperidinoalkyl) and (hydroxypyrrolidinoalkyl) aminosulfonyl]-6-nitrobenzoic acids are disclosed to have activity in increasing the sensitivity of hypoxic tumor cells to therapeutic radiation. Also disclosed are methods of preparing such compounds, pharmaceutical compositions including such compounds and methods of treating patients in need of therapeutic radiation with effective amounts of such compounds.

7 Claims, No Drawings

AMIDES AND ESTERS OF 2-(N-(HYDROXYPIPERIDINOALKYL) AND (HYDROXYPYRROLIDINOALKYL)-AMINOSULFONYL)-6-NITROBENZOIC ACIDS USEFUL AS ADJUNCTS TO RADIATION THERAPY

This is a continuation of application Ser. No. 795,567 filed Nov. 6, 1985, now abandoned.

BACKGROUND OF THE INVENTION

This invention relates to esters, amides and N-substituted amides of 2-[N-(hydroxypiperidinoalkyl) and (hydroxypyrrolidinoalkyl)aminosulfonyl]-6-nitrobenzoic acids which are useful as sensitizers of hypoxic tumor cells to therapeutic radiation. It also relates to pharmaceutical formulations comprising one of such compounds and a non-toxic pharmaceutically acceptable carrier and to the use of an effective amount of said compounds which comprises administering an effective amount of such compound to patients in need of such radiation treatment.

At the present time, certain other unrelated compounds are in experimental clinical use as radiation sensitizers. However, these compounds—for example, metronidazol and misonidazole—suffer from the drawback that they also cause neurotoxicity which limits their usefulness. The compounds of the present invention are effective radiation sensitizers and are believed to have a more favorable therapeutic ratio.

DETAILED DESCRIPTION OF THE INVENTION

The compositions of the present invention comprise a compound of the formula:

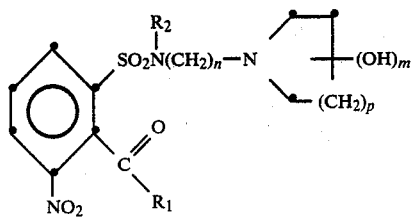

wherein:
$R_1$ is hydroxy(loweralkoxy), lower alkoxy, allyloxy, amino, alkylamino, di(loweralkyl)-amino, (hydroxyalkyl)amino, di(hydroxyalkyl)amino or allylamino;
$R_2$ is hydrogen, lower alkyl from 1-4 carbon atoms, hydroxyloweralkyl, allyl;
n is 2 or 3;
m is 0, 1 or 2;
p is 1 or 2 and in the above definitions alkyl is intended to mean a 1-4 carbon branched or straight chan alkyl group.

The compounds of this invention may be prepared by alkylation of the hydroxypiperidine or hydroxypyrrolidine with an amide or ester of formula III as shown in the following reaction scheme:

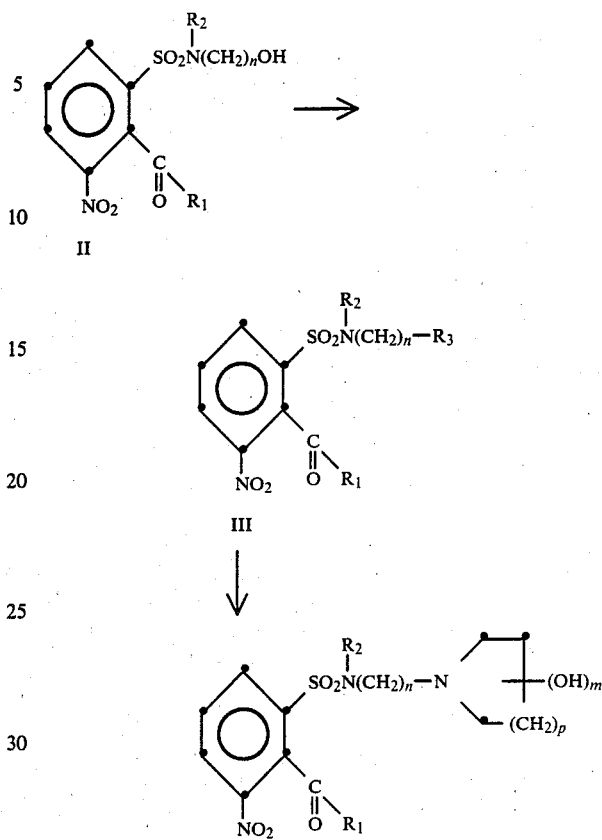

$R_1$, $R_2$, n, m and p are as defined hereinabove and $R_3$ is a displaceable group such as halogen, alkylsulfonyloxy or arylsulfonyloxy.

The reaction is carried out in a suitable aprotric solvent such as dimethylformamide, acetonitrile or the like. The reaction temperature may vary from 50° C. to the boiling point of the solvent for a period of 1 to 10 days. It is preferred to carry out the reaction in the presence of a base in sufficient amount to neutralize the acid formed in the course of the reaction. The base may be a tertiary amine such as a trialkylamine or pyridine. Alternatively, at least twice the molar amount of reactant amine theoretically required may be used. In this event, the reactant amine is utilized both to form the desired product and to neutralize the acid formed in the amination reaction.

The alkylating agents of formula III are readily prepared from the corresponding alcohols by established methods.

Note: these alcohols are described in U.S. patent application having Ser. No. 795,564 filed on the same date as the present application by Walfred Saari]

The compounds of this invention may also be prepared by reaction of a 6-nitrobenzoate ester or 6-nitrobenzamide having a 2-chlorosulfonyl substituent with at least an equimolar amount of an amine of formula

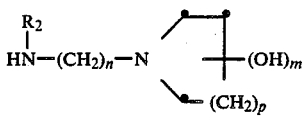

wherein $R_2$, n, m, and p are as described hereinabove.

It is preferred to carry out the reaction in the presence of a base in sufficient amount to neutralize the hydrogen chloride formed in the course of the reaction. The base utilized may be a tertiary amine such as triethylamine or pyridine. On the other hand the same results may be produced by adding at least twice the molar amount of reactant amine theoretically required. In this event, the reactant amine is utilized both to form the sulfonamide and to neutralize the hydrogen chloride formed in the amination reaction.

The temperature at which the reaction is carried out is not critical and may vary from 0°–100° C. or at the reflux temperature of the solvent, if under 100° C. The reaction temperature is preferably maintained at about 0°–25° C. for a period of 1–24 hours. The amination reaction may be formulated as follows:

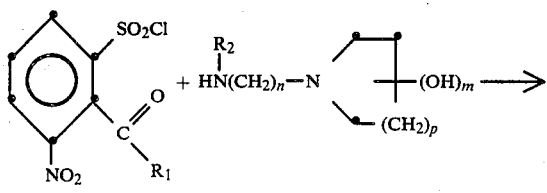

The benzamide derivatives of this invention may also be prepared by reaction of a 2-(monosubstituted sulfamyl)-6-nitrobenzoate ester with at least one equivalent of ammonia or a mono- or dialkylsubstituted amine. This amination reaction may be formulated as follows:

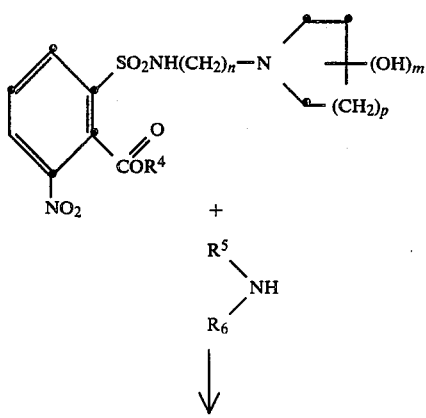

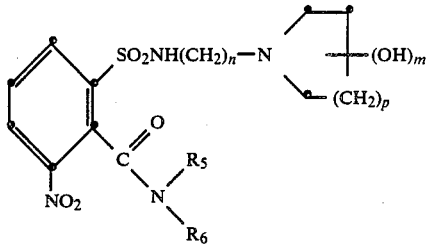

where n, m and p are as defined hereinabove, $R_4$ is either loweralkyl or hydroxy(loweralkyl). $R_5$ and $R_6$ may be hydrogen, loweralkyl from 1–4 carbon atoms, hydroxyalkyl, or allyl.

The reaction is carried out in a suitable solvent such as a lower aliphatic alcohol or a polar aprotic solvent such as dimethylformamide, dimethylsulfoxide or others such as tetrahydrofuran, glyme, or diglyme. The reaction temperature is not critical and may vary from 0°–100° C., preferably from about 25°–50° C. for a period of 1 to 10 days. When low boiling amines are used, the reaction may be run in a sealed vessel.

The following examples are intended to illustrate but not to limit the process of preparation, products, compositions or methods of treatment aspects of the invention. Temperatures are in degrees Celsius unless otherwise indicated throughout the specification. The term "alkyl" is intended to include only lower alkyl of 1–4 carbon atoms either straight or branched chain.

EXAMPLE 1

N,N-Dimethyl-2-[N-methyl-N-(2-(4-hydroxypiperidino)-ethyl)aminosulfonyl]-6-nitrobenzamide hydrogen oxalate Step A:
N,N-Dimethyl-2-[N-(2-methylsulfonyloxyethyl)-N-methylaminosulfonyl]-6-nitrobenzamide Methanesulfonyl chloride (0.24 ml) was added to a solution of N,N-dimethyl-2-[N-(2-hydroxyethyl)-N-methylaminosulfonyl]-6-nitrobenzamide (500 mg, 1.51 mmol) in dry pyridine (5 ml) and the reaction mixture was stirred at 20°–25° for 4 hours. After concentrating under reduced pressure, the residue was partitioned between EtOAc and 1N HCl. The organic extract was washed (saturated NaCl solution), dried ($Na_2SO_4$), filtered and concentrated. The crude product was flash chromatographed over silica gel and eluted with $CHCl_3$ to give pure mesylate (600 mg, 97%) as an oil.

Step B:
N,N-Dimethyl-2-[N-methyl-N-(2-(4-hydroxypiperidino)ethyl)aminosulfonyl]-6-nitrobenzamide hydrogen oxalate A solution of the mesylate (310 mg, 0.76 mmol) and 4-hydroxypiperidine (0.23 g, 2.3 mmol) in THF (20 ml) was stirred at reflux for 2.5 days and then concentrated under reduced pressure. The residue was partitioned between EtOAc and a saturated aqueous NaCl solution. After drying the EtOAc extract over $Na_2SO_4$, filtering and concentrating, the residue was flash chromatographed over silica gel. Product was eluted with 10% MeOH-90% $CHCl_3$ and purified by recrystallization of the hydrogen oxalate salt, m.p. 176.5°–178.0° dec, from MeOH-EtOAc-hexane.

EXAMPLE 2

Methyl 2-[N-(2-(4-Hydroxypiperidino)ethyl)aminosulfonyl]-6-nitrobenzoate

Step A: 4-Hydroxy-1-[2-(propionylamino)ethyl]-piperidine

A mixture of N-(2-chloroethyl)propanamide (27.1 g, 0.20 mol), 4-hydroxypiperidine (20.2 g, 0.20 mol) and anhydrous sodium carbonate (10.6 g, 0.10 mol) in acetonitrile (120 ml) was stirred at reflux under nitrogen for 20 hours. Additional 4-hydroxypiperidine (20.2 g, 0.20 mol) was added and the mixture stirred at reflux for 3 days. After concentrating under reduced pressure, the residue was dissolved in ethyl acetate and a minimum amount of water. The aqueous layer was saturated with sodium chloride and re-extracted several times with ethyl acetate. The organic extracts were combined, dried ($Na_2SO_4$), filtered and concentrated to give 13.1 g of crude product. Pure product was obtained by flash chromatography over silica gel and elution with 20% methanol-80% chloroform.

Step B: 1-(2-Aminoethyl)-4-hydroxypiperidine dihydrochloride

A solution of 4-hydroxy-1-[2-(propionylamino)ethyl]piperidine (1.7 g, 8.5 mmol) in 10% hydrochloric acid was stirred at reflux for 20 hours and then concentrated under reduced pressure. The residue was triturated with ethylacetate and the insoluble solid recrystallized from methanol-ethylacetate to give 1.3 g of the dihydrochloride salt, m.p. 186°–188° C.

Step C: Methyl 2-[N-(2-(4-hydroxypiperidino)ethyl)-amino)sulfonyl]-6-nitrobenzoate A solution of methyl 2-chlorosulfonyl-6-nitrobenzoate (1.5 g, 5.4 mmol) in tetrahydrofuran (100 ml) was added over 1 hour to a stirred mixture of 1-(2-aminoethyl)-4-hydroxypiperidine dihydrochloride (1.2 g, 5.4 mmol) and triethylamine (2.3 ml, 16.5 mmol) in tetrahydrofuran (75 ml) cooled in an ice bath. After stirring at room temperature for 6 hours, solvent was removed under reduced pressure and the residue partitioned between ethyl acetate and saturated sodium chloride solution. The ethyl acetate extract was dried ($Na_2SO_4$), filtered and concentrated. The residue was flash chromatographed on silica gel and eluted with 5% methanol-95% chloroform to give pure product, 1.0 g, as an oil.

EXAMPLE 3

N,N-Dimethyl 2-[N-(2-(4-hydroxypiperidino)ethyl)aminosulfonyl]-6-nitrobenzamide hydrogen oxalate A solution of methyl 2-[N-(2-(4-hydroxypiperidino)ethyl)aminosulfonyl]-6-nitrobenzoate (1.0 g, 2.6 mmol) and 40% aqueous dimethylamine solution (3.0 ml) in methanol (50 ml) was stirred at 20°–25° for 3 days. After concentrating under reduced pressure, residue was partitioned between ethyl acetate and saturated sodium bicarbonate solution. The ethyl acetate extract was washed with saturated sodium chloride solution, dried ($Na_2SO_4$), filtered and concentrated. The residue was flash chromatographed over silica gel and eluted with 7% methanol 93% chloroform to give 800 mg of pure product as an oil. The base was converted to the hydrogen oxalate salt with oxalic acid and recrystallized from methanol-ethyl acetate-hexane to give analytically pure material, m.p. 80° dec.

Example 4

N,N-Dimethyl 2-[N-methyl-N-(2-(3-hydroxypiperidino)ethylaminosulfonyl]-6-nitrobenzamide Hydrogen Fumarate A solution of N,N-dimethyl 2-[N-(2-methylsulfonyloxyethyl)-N-methylaminosulfonyl]-6-nitrobenzamide (0.43 g, 1.05 mmol) and 3-hydroxypiperidine (0.31 g, 3.06 mmol) in acetonitrile (40 ml) was stirred at reflux for 1 day. After concentrating under reduced pressure, the residue was partitioned between ethyl acetate and a saturated aqueous solution of sodium chloride. The ethyl acetate extract was dried ($Na_2SO_4$), filtered and concentrated. Flash chromatography of the residue over silica gel and elution with 5% methanol −95% methylene chloride gave 400 mg of pure product as an oil. The hydrogen fumarate salt, m.p. 132°–35° dec, was prepared for analysis.

EXAMPLE 5

N,N-Dimethyl 2-[N-Methyl-N-(2-(3-hydroxypyrrolidino)ethylaminosulfonyl]-6-nitrobenzamide.

A solution of N,N-dimethyl 2-[N-(2-methylsulfonyloxyethyl)-N-methylaminosulfonyl]-6-nitrobenzamide (0.70 g, 1.7 mmol) and 3-pyrrolidinol (0.30 g, 3.4 mmol) in acetonitrile (30 ml) was stirred at reflux for 1 day. After concentrating under reduced pressure, the residue was partitioned between ethyl acetate and a saturated aqueous solution of sodium chloride. The ethyl acetate extract was dried ($Na_2SO_4$), filtered and concentrated to 0.44 g of oily product, homogeneous tlc (5% methanol-95% chloroform, silica gel), $R_f = 0.10$.

What is claimed is:

1. A compound of the formula:

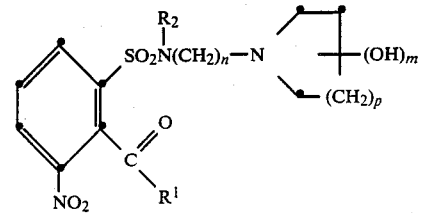

wherein:

$R_1$ is hydroxy(loweralkoxy), lower alkoxy, allyloxy, amino, alkylamino, di(loweralkyl)amino, (hydroxyalkyl)amino, di(hydroxy-alkyl)amino or allylamino;

$R_2$ is hydrogen, lower alkyl from 1–4 carbon atoms, hydroxyloweralkyl, allyl;

n is 2 or 3;

m is 0, 1 or 2;

p is 1 or 2 and pharmaceutically acceptable salts thereof.

2. A method for enhancing the therapeutic effect of radiation which comprises administering to a patient in need of such radiation treatment an effective amount of a compound defined in claim 1.

3. A pharmaceutical composition for enhancing the therapeutic effect of radiation which consists of an effective amount of a compound defined in claim 1 and a non-toxic pharmaceutically acceptable carrier.

4. A compound according to claim 1 which is N,N-dimethyl-2-[N-methyl-N-(2-(4-hydroxypiperidino)ethyl)aminosulfonyl]-6-nitrobenzamide.

5. A compound according to claim 1 which is methyl 2-[N-(2-(4-hydroxypiperidino)ethyl]aminosulfonyl]-6-nitrobenzoate.

6. A compound according to claim 1 which is N,N-dimethyl-2-[N-(2-(4-hydroxypiperidino)ethyl]aminosulfonyl]-6-nitrobenzamide.

7. A compound according to claim 1 which is N,N-dimethyl-2-[N-(2-(3-hydroxypyrrolidino)ethyl)-N-methylaminosulfonyl]-6-nitrobenzamide.

* * * * *